(12) United States Patent
Butters et al.

(10) Patent No.: US 8,975,280 B2
(45) Date of Patent: Mar. 10, 2015

(54) DEOXYNOJIRIMYCIN AND D-ARABINITOL ANALOGS AND METHODS OF USING

(75) Inventors: Terry D. Butters, Oxford (GB); Raymond A. Dwek, Oxford (GB); George W. J. Fleet, Oxford (GB)

(73) Assignee: The Chancellor, Masters and Scholars of The University of Oxford, Oxford (GB)

( * ) Notice: Subject to any disclaimer, the term of this patent is extended or adjusted under 35 U.S.C. 154(b) by 1252 days.

(21) Appl. No.: 11/752,015

(22) Filed: May 22, 2007

(65) Prior Publication Data

US 2007/0275998 A1    Nov. 29, 2007

Related U.S. Application Data

(60) Provisional application No. 60/802,776, filed on May 24, 2006.

(51) Int. Cl.
*A61K 31/445* (2006.01)
*C07D 211/48* (2006.01)
*C07D 211/46* (2006.01)

(52) U.S. Cl.
CPC ............ *C07D 211/48* (2013.01); *C07D 211/46* (2013.01)
USPC ........... 514/317; 514/151; 514/315; 546/216; 546/219

(58) Field of Classification Search
CPC .. A61K 31/445; C07D 211/46; C07D 211/48; C07D 211/54
USPC ................... 514/315, 317, 151; 546/219, 216
See application file for complete search history.

(56) References Cited

U.S. PATENT DOCUMENTS

| | | | |
|---|---|---|---|
| 4,407,809 A | 10/1983 | Junge et al. | |
| 4,533,668 A | 8/1985 | Matsumura et al. | |
| 4,639,436 A | 1/1987 | Junge et al. | |
| 4,871,747 A | 10/1989 | Kinast et al. | |
| 4,985,445 A | 1/1991 | Tsuruoka et al. | |
| 5,051,407 A | 9/1991 | Boshagen et al. | |
| 5,256,788 A | 10/1993 | Ezure et al. | |
| 6,809,083 B1 | 10/2004 | Mueller et al. | |
| 2006/0264467 A1 | 11/2006 | Mugrage et al. | |

FOREIGN PATENT DOCUMENTS

| | | |
|---|---|---|
| DE | 3024901 A1 | 1/1982 |
| EP | 0 000 947 A1 | 3/1979 |
| EP | 0 350 012 A2 | 1/1990 |
| EP | 0 449 026 A2 | 10/1991 |
| EP | 0 536 402 A1 | 4/1993 |
| JP | 54-046786 A | 4/1979 |
| JP | 54-106477 A | 8/1979 |
| JP | 55-047655 A | 4/1980 |
| JP | 62-155291 A | 7/1987 |
| JP | 04-262791 A | 9/1992 |
| JP | 2003-522791 A | 7/2003 |
| WO | WO 92/00277 A1 | 1/1992 |
| WO | WO 92/05152 A2 | 4/1992 |

(Continued)

OTHER PUBLICATIONS

Rawling et al. "Synthesis and biological . . . " ChemBioChem v.10, p. 1101-1105 (2009).*
Matsumura et al. "Moranoline deriavatives" CA 92:147138 (1980).*
Meuller et al. "Use of N-substuted . . . " CA 131:165293 (1999).*
Glycosidehydrolase family, Wikipedia, p. 1-20 (2011).*
Olesen "The use of . . . " Curr. Opin. Drug discovery and develop. v.4(4) p. 471-478 (2001).*
Bird et al. "Intramolecular restions . . . " CA79:77660 (1973).*
Fed. Register "examination guidelines update: . . . " p. 1-34 from internet (2011).*
Junge et al. "3m4m5-trihydroxy . . . " CA96:7033 (1982).*
Nippon Shinyaku "Moranoline . . . " CA96:19981 (1982).*
Maruo S. "Novel manufacturing . . . " CA119:224290 (1993).*
Olesen "The use of . . . " Curr. Opin. Drug discovery and develop, v.4(4) p. 471-478 (2001).*
King "Bioisosters . . . " Med. Chem: Principle & Practive p. 206-209 (1994).*
Patani et al. "Bioisosterism: a rational . . . " Chem. Rev. v.96, p. 3147-3176 (1996).*

(Continued)

*Primary Examiner* — Celia Chang
(74) *Attorney, Agent, or Firm* — Foley & Lardner LLP

(57) ABSTRACT

A compound of Formula I are provided:

wherein R is:

$R_1$ is a substituted or unsubstituted alkyl group; $W_{1-4}$ are independently selected from hydrogen, substituted or unsubstituted alkyl groups, substituted or unsubstituted haloalkyl groups, substituted or unsubstituted alkanoyl groups, substituted or unsubstituted aroyl groups, or substituted or unsubstituted haloalkanoyl groups; $X_{1-5}$ are independently selected from H, $NO_2$, $N_3$, and $NH_2$; Y is absent or is a substituted or unsubstituted $C_1$-alkyl group, other than carbonyl; Z is selected from a bond or NH, provided that when Z is a bond, Y is absent, and provided that when Z is NH, Y is a substituted or unsubstituted $C_1$-alkyl group, other than carbonyl. Also provided are D-arabinitol compounds, methods for preparing such compounds and compositions of such compounds, and methods of using such compounds.

38 Claims, 2 Drawing Sheets

(56) References Cited

FOREIGN PATENT DOCUMENTS

| WO | WO 95/19172 A1 | 7/1995 |
|----|----------------|--------|
| WO | WO 95/22975 A1 | 8/1995 |
| WO | WO 99/24401 A1 | 5/1999 |
| WO | WO 01/60366 A1 | 8/2001 |
| WO | WO 02/055498 A1 | 7/2002 |

OTHER PUBLICATIONS

"After KSR guidelines" Fed. Regster v.75, p. 53643-53660 (2010).*
Berg et al. "Biochemistry" Chapger 8, section 8.5, p. 1-7 (2002).*
International Preliminary Report on Patentability and Written Opinion for PCT/US2007/069448 dated Dec. 11, 2008.
G. B. Karlsson et al., "Effects of the Imino Sugar N-Butyldeoxynojirimycin on the N-Glycosylation of Recombinant gp120," 268 J. Biol. Chem., 570-576 (1993).
D. C. Neville et al, "Analysis of Fluorescently Labeled Glycosphingolipid-Derived Oligosaccharides Following Ceramide Glycanase Digestion and Anthranilic Acid Labeling," 331, Anal. Biochem. 275-282 (2004).
H. R. Mellor et al., "Preparation, Biochemical Characterization and Biological Properties of Radiolabelled N-alkylated Deoxynojirimycins," 336 Biochem. J. 225-233 (2002).
H. R. Mellor et al., "Cellular Effects of Deoxynojirimycin Analogues: Inhibition of N-Linked Oligosaccharide Processing and Generation of Free Glucosylated Oligosaccharides," 381 Biochem. J. 867-875 (2004).
H. R. Mellor et al., "Cellular Effects of Deoxynojirimycin Analogues: Uptake, Retention and Inhibition of Glycosphingolipid Biosynthesis," 381 Biochem. J. 861-866 (2004).
R. A. Dwek et al., "Targeting Glycosylation as a Therapeutic Approach, 1 Nat. Rev. Drug Discov.," 65-75 (2002).
A. Saint-Pol et al., "Cytosol-to-lysosome Transport of Free Polymannose-type Oligosaccharides," 274 J. Biol. Chem. 13547-13555 (1999).
T. Suzuki et al., "Endo-β-N-acetylglucosaminidase, an Enzyme Involved in Processing of Free Oligosaccharides in the Cytosol," 99 Proc. Natl. Acad. Sci. USA 9691-9696 (2002).
V. A. Shoup et al., "Purification and Characterization of the a-D-Mannosidase of Rat Liver Cytosol," 251 J. Biol. Chem. 3845-3852 (1976).
G. Li et al., "Multiple Modes of Interaction of the Deglycosylation Enzyme, Mouse Peptide N-glycanase, with the Proteasome," 102 Proc. Natl. Acad. Sci. USA 15809-15814 (2005).
Spiro, R. G., "Role of N-linked Polymannose Oligosaccharides in Targeting Glycoproteins for Endoplasmic Reticulum-associated Degradation," 61 Cell Mol. Life Sci. 1025-1041 (2004).
E. J. Wiertz et al., "Sec61-mediated Transfer of a Membrane Protein from the Endoplasmic Reticulum to the Proteasome for Destruction," 384 Nature 432-438 (1996).
S.E. Moore et al., "Demonstration That Golgi Endo-α-D-mannosidase Provides a Glucosidase-independent Pathway for the Formation of Complex N-Linked Oligosaccharides of Glycoproteins," 265 J. Biol. Chem. 13104-13112 (1990).
K. Fujimoto, K. et al., "α-Glucosidase II-deficient Cells Use Endo α-Mannosidase as a Bypass Route for N-Linked Oligosaccharide Processing," 266 J. Biol. Chem. 3571-3578 (1991).
R. G. Spiro et al., "Definition of the Lectin-like Properties of the Molecular Chaperone, Calreticulin, and Demonstration of Its Copurification with Endomannosidase from Rat Liver Golgi," 271 J. Biol. Chem. 11588-11594 (1996).
L. A. van den Broek et al., "Synthesis of Oxygen-Substituted N-alkyl 1-Deoxynojirimycin Derivatives: Aza Sugar α-Glucosidase Inhibitors Showing Antiviral (HIV-1) and Immunosuppressive Activity," 113 Recueil des Travaux Chimiques des Pays-Bas 507-516. (1994).
T. D. Butters et al., "Molecular Requirements of Imino Sugars for the Selective Control of N-Linked Glycosylation and Glycosphingolipid Biosynthesis," 11 Tetrahedron: Asymmetry 113-124 (2000).
International Search Report and Written Opinion for PCT/US2007/069448 dated Sep. 23, 2008.
Matsumara, S. et al., Database CAPLUS on STN (Columbus, OH, USA), No. 92:147138 "moranoline derivatives," Abstract (1980).
Romaniouk, Andrew V. et al., Database CAPLUS on STN (Columbus, OH, USA), No. 141:407749, "Synthes of a novel photoaffinity derivative," Abstract (2004).
Office Action dated Nov. 5, 2010), in corresponding Chinese application 200780027372.1, 12 pages.
Huang et al. "Antiviral activity of some natural and synthetic sugar analogues," FEBS Letters, Oct. 1991, 291(2):199-202.
Huang et al., "Antiviral activity of some natural and synthetic sugar analogs," Database Caplus [Online], XP002692804, Database accession No. 1992:98886, abstract, one page.
Le Merrer et al., "Synthesis of Azasugars as Potent Inhibitors of Glycosidases," Bioorganic & Medicinal Chemistry, Mar. 1, 1997, 5(3):519-533.
Matsumura et al. "Moranoline derivatives," Database Caplus [Online], Chemical Abstracts Service, Columbus, Ohio, XP002692803, Database accession No. 1980:42339 (abstract of JP 54-105477).
Mehta et al., "Imino sugars that are less toxic but more potent as antivirals, in vitro, compared with N-n-nonyl DNJ," Antiviral Chemistry & Chemotherapy, Sep. 1, 2002, 13(5):299-304.
Van den Broek et al., "Chemical modification of azasugars, inhibitors of N-glycoprotein-processing glycosidases and of HIV-1 infection," Recl. Trv. Chim. Pays-Bas, Jan. 1, 1993, 112:82-94.
Shiozaki et al., "Synthesis of 1-Deoxynojirimycin-Trehalamine Fused Compound and Its Related Compounds," Tetrahedron Letters, 1998, 39;1925-1928.
Fleet et al., "Inhibition of HIV replication by amino-sugar derivatives," FEBS Letters, Sep. 1988, 237(1,2)_128-132.
Chery et al., "Synthesis of peptidomimetics based on iminosugar and β-D-glucopyranoside scaffolds and inhibition of HIV-protease," Tetrahedron, 2004, 60:6597-6608.
Fowler et al., "Synthesis and activity towards yeast α-glucosidase of 1,5-dideoxy-1,5-imino-L-iditol (1-deoxy-L-idonojirimycin)," Carbohydrate Research, 1993, 246:377-381.
Mehta et al., "A norbonyl route to azasugars: a new synthesis of deoxynojirimycin analogues," Tetrahedron Letters, 2000, 41:5741-5745.
Tan et al., "Chemical Modification of the Glucosidase Inhibitor 1-Deoxynojirimycin," The Journal of Biological Chemistry, Aug. 5, 1991, 266(22):14504-14510.

* cited by examiner

DEOXYNOJIRIMYCIN AND D-ARABINITOL ANALOGS AND METHODS OF USING

CROSS-REFERENCE TO RELATED APPLICATION

This application claims the benefit of U.S. Provisional Application No. 60/802,776 filed May 24, 2006, the entire contents of which is incorporated herein by reference.

FIELD OF THE INVENTION

The present invention generally relates to N-alkylated imino sugar analogs, their preparation, and their use. More specifically, embodied are analogs of deoxynojirimycin and D-arabinitol, novel methods of preparing, compositions containing, and the use of such analogs.

BACKGROUND

Deoxynojirimycin (DNJ) and certain N-alkylated modifications of this compound are potent endoplasmic reticulum (ER) α-glucosidase I and II inhibitors. (T. D. Butters, et al. *Molecular Requirements of Imino Sugars for the Selective Control of N-Linked Glycosylation and Glycosphingolipid Biosynthesis*, 11 Tetrahedron: Asymmetry 113-124 (2000).) Imino sugars quickly and efficiently cross the plasma membrane such that the concentration of imino sugars in the cytosol is at equilibrium with the extracellular concentration. (H. R. Mellor, et al., *Cellular Effects of Deoxynojirimycin Analogues: Uptake, Retention and Inhibition of Glycosphingolipid Biosynthesis*, 381 Biochem. J. 861-866 (2004).)

In the cytosol, imino sugars directly interact with the ceramide-specific glucosyltransferase on the cytosolic side of the cis-Golgi inhibiting glycolipid biosynthesis. However, to modulate N-linked processing by glucosidase inhibition, imino sugars have to gain entry to the ER lumen. The rate of entry into the ER is unknown, but the concentration of imino sugar is assumed to be much lower in the ER lumen than is supplied exogenously to the cell. Evidence for this comes from experiments where the concentration required to inhibit ER glucosidase I has been measured, often requiring 1,000-10,000 times that which inhibits the purified enzyme in vitro. (L. A. van den Broek, et al., *Synthesis of Oxygen-Substituted N-alkyl 1-Deoxynojirimycin Derivatives: Aza Sugar α-Glucosidase Inhibitors Showing Antiviral (HIV-1) and Immunosuppressive Activity*, 113 Recueil des Travaux Chimiques des Pays-Bas 507-516. (1994).)

Following access to the lumen of the ER, DNJ analogues inhibit the removal of glucose residues, mediated by α-glucosidases I and II, forming proteins containing hyperglucosylated N-linked oligosaccharides that may fail to interact with the chaperones calnexin and calreticulin, both of which are involved in protein folding quality control. (R. G. Spiro, et al., *Definition of the Lectin-like Properties of the Molecular Chaperone, Calreticulin, and Demonstration of Its Copurification with Endomannosidase from Rat Liver Golgi*, 271 J. Biol. Chem. 11588-11594 (1996).) Some proteins with hyperglucosylated glycans may still be processed in the Golgi by an endo-α(1,2)mannosidase, thus circumventing the block in oligosaccharide processing caused by glucosidase inhibition. (K. Fujimoto, K., et al., *α-Glucosidase II-deficient Cells Use Endo α-Mannosidase as a Bypass Route for N-Linked Oligosaccharide Processing*, 266 J. Biol. Chem. 3571-3578 (1991); S. E. Moore, et al., *Demonstration That Golgi Endo-α-D-mannosidase Provides a Glucosidase-independent Pathway for the Formation of Complex N-Linked Oligosaccharides of Glycoproteins*, 265 J. Biol. Chem. 13104-13112 (1990).)

The removal of misfolded protein from the ER and production of free oligosaccharides (FOS) is a normal cellular process. Calnexin- or calreticulin-dependent, aberrantly-folded protein and hyperglucosylated, aberrantly-folded proteins are ultimately translocated out of the ER into the cytosol via the Sec61p channel (E. J. Wiertz, et al., *Sec61-mediated Transfer of a Membrane Protein from the Endoplasmic Reticulum to the Proteasome for Destruction*, 384 Nature 432-438 (1996)), where the N-linked oligosaccharide is released by a cytosolic peptide: N-glycanase (PNGase) (which may or may not be in direct interaction with the Sec61p channel) producing FOS. (G. Li, et al., *Multiple Modes of Interaction of the Deglycosylation Enzyme, Mouse Peptide N-glycanase, with the Proteasome*, 102 Proc. Natl. Acad. Sci. USA 15809-15814 (2005); Spiro, R. G., *Role of N-linked Polymannose Oligosaccharides in Targeting Glycoproteins for Endoplasmic Reticulum-associated Degradation*, 61 Cell Mol. Life Sci. 1025-1041 (2004).) This process of selective protein export from the ER to the cytosol followed by proteasomal degradation is known as ER-associated degradation (ERAD). FOS produced in the cytoplasm are acted upon by cytosolic enzymes such as endo-R-Nacetylglucosaminidase (EnGNase) (T. Suzuki, et al., *Endo-β-N-acetylglucosaminidase, an Enzyme Involved in Processing of Free Oligosaccharides in the Cytosol*, 99 Proc. Natl. Acad. Sci. USA 9691-9696 (2002)) and cytosolic α-mannosidase (V. A. Shoup, et al., *Purification and Characterization of the α-D-Mannosidase of Rat Liver Cytosol*, 251 J. Biol. Chem. 3845-3852 (1976)), ultimately forming a $Man_5GlcNAc_1$ (M5N) species that is transported to the lysosome. However, glucosylated FOS are allegedly not able to gain entry to the lysosome for degradation (A. Saint-Pol, et al., *Cytosol-to-lysosome Transport of Free Polymannose-type Oligosaccharides*, 274 J. Biol. Chem. 13547-13555 (1999)), and their fate remains to be determined. Other small, but detectable, amounts of FOS including $Glc_1Man_5GlcNAc_1$ are present in cells, in addition to M5N, representing the normal default pathway for ERAD. (H. R. Mellor et al., *Cellular Effects of Deoxynojirimycin Analogues: Inhibition of N-Linked Oligosaccharide Processing and Generation of Free Glucosylated Oligosaccharides*, 381 Biochem. J. 867-875 (2004).)

The development of a cellular-based ER α-glucosidase assay that determines the rate of α-glucosidase-mediated hydrolysis of N-linked oligosaccharides, as proteins are folded in the ER in the presence of inhibitor, reveals important principles of oligosaccharide intermediates in the biosynthetic pathway and can be used to predict efficacy for protein misfolding; a strategy that has been proposed as a potential therapy for the inhibition of viral infectivity. (R. A. Dwek, et al., *Targeting Glycosylation as a Therapeutic Approach*, 1 Nat. Rev. Drug Discov. 65-75 (2002).)

SUMMARY

In one aspect, novel imino sugar compounds of Formula I and II are provided:

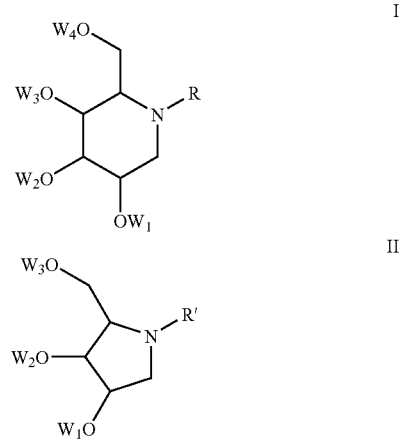

wherein R is:

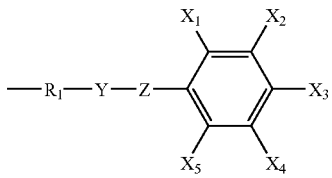

R' is:

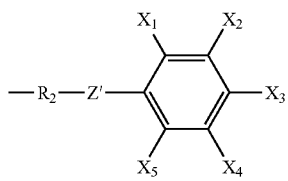

$R_1$ is a substituted or unsubstituted alkyl group;
$R_2$ is a substituted or unsubstituted alkyl group;
$W_{1-4}$ are independently selected from hydrogen, substituted or unsubstituted alkyl groups, substituted or unsubstituted haloalkyl groups, substituted or unsubstituted alkanoyl groups, substituted or unsubstituted aroyl groups, or substituted or unsubstituted haloalkanoyl groups;
$X_{1-5}$ are independently selected from H, $NO_2$, $N_3$, or $NH_2$;
Y is absent or is a substituted or unsubstituted $C_1$-alkyl group, other than carbonyl;
Z is selected from a bond or NH;
  provided that when Z is a bond, Y is absent, and
  provided that when Z is NH, Y is a substituted or unsubstituted $C_1$-alkyl group, other than carbonyl; and
Z' is a bond or NH.

In another aspect, methods for preparing compounds of Formula III are provided comprising:

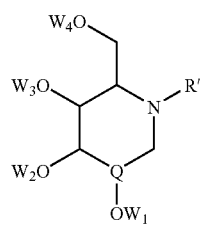

condensing a compound of Formula IV:

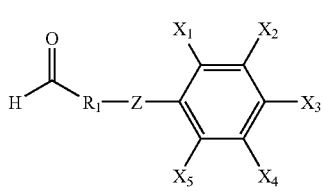

with a compound of Formula V

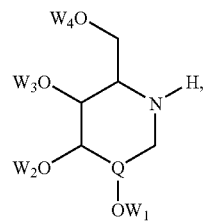

wherein,
R' is:

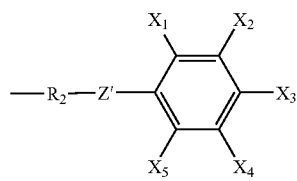

Q is absent or is CH,
  provided that if Q is absent $OW_1$ is also absent.
$R_2$ is a substituted or unsubstituted alkyl group;
$W_{1-4}$ are independently selected from hydrogen, substituted or unsubstituted alkyl groups, substituted or unsubstituted haloalkyl groups, substituted or unsubstituted alkanoyl groups, substituted or unsubstituted aroyl groups, or substituted or unsubstituted haloalkanoyl groups;
$X_{1-5}$ are independently selected from H, $NO_2$, $N_3$, or $NH_2$; and
Z' is selected from a bond or NH.

In another aspect, methods for inhibiting an α-glucosidase with a compound of Formula I, Formula II, Formula III, a salt thereof, or a mixture of any two or more thereof are provided.

In yet another aspect, methods for inhibiting removal of glucose residues from an oligosaccharide by contacting an α-glucosidase with a compound of Formula I, Formula II, Formula III, a salt thereof, or a mixture of any two or more thereof are provided.

In another aspect, methods are provided for inhibiting a virus infecting a mammal comprising contacting a mammalian cell infected with a virus, with a compound of Formula I, a compound of Formula II, a compound of Formula III, a pharmaceutically acceptable salt thereof, or a mixture of any two or more thereof, in an amount effective to inhibit the virus.

DETAILED DESCRIPTION

Figure 1:
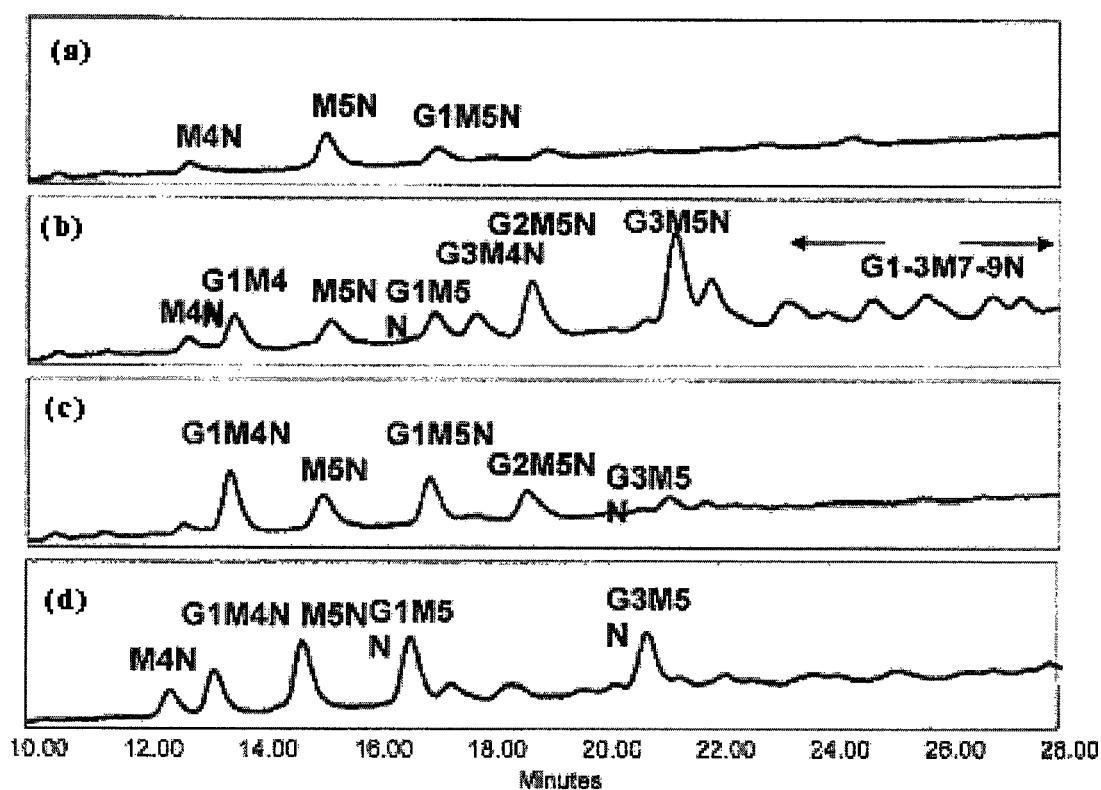
FIG. 1 shows NP-HPLC results for FOS isolated from control cells (a); NAP-DNJ (50 μM) treated cells (b); DNP-DNJ (50 μM) treated cells (c), and NB-DNJ (1 mM) treated cells (d).

"AA" is an abbreviation for anthranilic acid.
"DNJ" is an abbreviation for deoxynojirimycin.
"ER" is an abbreviation for endoplasmic reticulum.

"ERAD" is an abbreviation for endoplasmic reticulum associated degradation.

"FOS" is an abbreviation referring to free oligosaccharides.

"NAP-DNJ" is an abbreviation for N—(N'-{4'azido-2'-nitrophenyl)-6-aminohexyl)-deoxynojirimycin.

"NDP-DNJ" is an abbreviation for N—(N'-{2,4-dinitrophenyl)-6-aminohexyl)-deoxynojirimycin.

"NP-HPLC" is an abbreviation for normal-phase high performance liquid chromatography.

"Tris" is an abbreviation for tris(hydroxymethyl)aminomethane.

As used herein, "photoaffinity labeling" refers to a technique in which a photochemically reactive species, specifically associated with a biomolecule, is photoexcited in order to covalently attach a label to the biomolecule, usually via intermediates.

In general, "substituted" refers to a functional group, as defined below, in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. In some embodiments, substituted groups have 1, 2, 3, 4, 5, or 6 substituents. Examples of substituent groups include, but are not limited to: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; ethers; urethanes; oximes; hydroxylamines; alkoxyamines; thiols; sulfides such as alkyl, alkenyl, alkynyl, aryl, aralkyl, heterocyclyl and heterocyclylalkyl sulfide groups; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; and nitriles.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups may also be substituted with alkyl, alkenyl, and alkynyl groups as defined below.

Alkyl groups include straight chain and branched alkyl groups and cycloalkyl groups having from 1 to about 20 carbon atoms in some embodiments, from 1 to 12 carbon atoms in other embodiments, and from 1 to 8 carbon atoms, in yet other embodiments. Examples of straight chain alkyl groups include, but are not limited to, those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, isopentyl, and 2,2-dimethylpropyl groups. Alkyl groups may be substituted or unsubstituted. Representative substituted alkyl groups may be substituted one or more times with any of the groups listed above, for example, amino, oxo, hydroxy, cyano, carboxy, nitro, thio, alkoxy, and F, Cl, Br, I groups.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 6, or 7. Cycloalkyl groups further include mono-, bicyclic and polycyclic ring systems, such as, for example bridged cycloalkyl groups as described below, and fused rings, such as, but not limited to, decalinyl, and the like.

Cycloalkyl groups may be substituted or unsubstituted. Substituted cycloalkyl groups may be substituted one or more times with non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4- 2,5- or 2,6-disubstituted cyclohexyl groups, which may be substituted with any of the groups listed above, for example, methyl, amino, hydroxy, cyano, carboxy, nitro, thio, alkoxy, and F, Cl, Br, I groups.

Alkenyl groups include straight and branched chain alkyl and cycloalkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to vinyl, CH═CH(CH$_3$), CH═C(CH$_3$)$_2$, C(CH$_3$)═CH$_2$, C(CH$_3$)═CH(CH$_3$), C(CH$_2$CH$_3$)═CH$_2$, cyclohexenyl, cyclopentenyl, cyclohexadienyl, butadienyl, pentadienyl, and hexadienyl, among others. Alkenyl groups may be substituted or unsubstituted.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$), among others Alkynyl groups may be substituted or unsubstituted.

Aryl groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Aryl groups may be substituted or unsubstituted. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with groups such as those listed above.

Heterocyclyl groups include aromatic (also referred to as heteroaryl) and non-aromatic ring compounds containing 3 or more ring members, of which one or more is a heteroatom such as, but not limited to, N, O, and S. In some embodiments, the heterocyclyl group contains 1, 2, 3, or 4 heteroatoms. In some embodiments, heterocyclyl groups include 3 to 20 ring members, whereas other such groups have 3 to 6, 10, 12, or 15 ring members. Heterocyclyl groups encompass unsaturated, partially saturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]-dioxinyl, and benzo[1,3]dioxolyl. The phrase also includes bridged polycyclic ring systems containing a heteroatom such as, but not limited to, quinuclidyl. However, the phrase does not include heterocyclyl groups that have other groups, such as alkyl, oxo or halo groups, bonded to one of the ring members. Rather, these are referred to as "substituted heterocyclyl groups." Heterocyclyl groups may be substituted or unsubstituted. Heterocyclyl groups include, but are not limited to, pyrrolidinyl, pyrrolinyl, imidazolyl, imidazolinyl, imidazolidinyl, piperidinyl, piperazinyl, morpholinyl, pyrrolyl, pyrazolyl, pyrazolidinyl, tetrahydropyranyl, thiomorpholinyl, pyranyl, triazolyl, tetrazolyl, furanyl, tetrahydrofuranyl, oxazolyl, isoxazolyl, thiazolyl, pyridinyl, pyrimidinyl, pyridazinyl, pyrazinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, quinazolinyl, benzotriazolyl, 2,3-dihydrobenzo[1,4]dioxinyl, and benzo[1,3]dioxolyl groups. Representative substituted heterocyclyl groups may be mono-substituted or substituted more than once, such as, but not limited to, pyridinyl or morpholinyl groups, which are 2-, 3-, 4-, 5-, or 6-substituted, or disubstituted with various groups as defined above, including, but not limited to, alkyl, oxo, carbonyl, amino, alkoxy, cyano, and/or halo.

Alkoxy groups are hydroxyl groups (—OH) in which the bond to the hydrogen atom is replaced by a bond to a carbon atom of an alkyl group as defined above. Examples of linear alkoxy groups include but are not limited to methoxy, ethoxy, propoxy, butoxy, pentoxy, hexoxy, and the like. Examples of branched alkoxy include but are not limited to isopropoxy, sec-butoxy, tert-butoxy, isopentoxy, isohexoxy, and the like. Examples of cyclic alkoxy include but are not limited to cyclopropyloxy, cyclobutyloxy, cyclopentyloxy, cyclohexyloxy, and the like. Representative substituted alkoxy groups may be substituted one or more times with various groups as defined above, including, but not limited to, amino, oxo, alkoxy, alkyl, cyano, and/or halogen groups.

The terms "aryloxy" and "arylalkoxy" refer to, respectively, an aryl group bonded to an oxygen atom and an aralkyl group bonded to the oxygen atom at the alkyl. Examples include but are not limited to phenoxy, naphthyloxy, and benzyloxy. Representative substituted aryloxy and arylalkoxy groups may be substituted one or more times with various groups as defined above, including, but not limited to, amino, oxo, alkoxy, alkyl, cyano, and/or halogen groups.

The term "carboxylate" as used herein refers to a —COOH group.

The term "carboxylic ester" as used herein refers to —COOR$^{30}$ groups. R$^{30}$ is a substituted or unsubstituted alkyl, cycloalkyl, alkenyl, alkynyl, aryl, aralkyl, heterocyclylalkyl or heterocyclyl group as defined herein.

The term "amide" (or "amido") includes C- and N-amide groups, i.e., —C(O)NR$^{31}$R$^{32}$, and —NR$^{31}$C(O)R$^{32}$ groups, respectively. R$^{31}$ and R$^{32}$ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups (—C(O)NH$_2$) and formamide groups (—NHC(O)H).

Urethane groups include N- and O-urethane groups, i.e., —NR$^{33}$C(O)OR$^{34}$ and —OC(O)NR$^{33}$R$^{34}$ groups, respectively. R$^{33}$ and R$^{34}$ are independently hydrogen, or a substituted or unsubstituted alkyl, alkenyl, alkynyl, cycloalkyl, aryl, aralkyl, heterocyclylalkyl, or heterocyclyl group as defined herein.

The term "amine" as used herein refers to —NHR$^{35}$ and —NR$^{36}$R$^{37}$ groups, wherein R$^{35}$, R$^{36}$ and R$^{37}$ are independently hydrogen, or a substituted or unsubstituted alkyl, alkenyl, alkynyl, cycloalkyl, aryl, aralkyl, heterocyclylalkyl or heterocyclyl group as defined herein. Unsubstituted amines are referred to as amino groups and have the formula —NH$_2$.

The term "sulfonamido" includes S- and N-sulfonamide groups, i.e., —SO$_2$NR$^{38}$R$^{39}$ and —NR$^{38}$SO$_2$R$^{39}$ groups, respectively. R$^{38}$ and R$^{39}$ are independently hydrogen, or a substituted or unsubstituted alkyl, alkenyl, alkynyl, cycloalkyl, aryl, aralkyl, heterocyclylalkyl, or heterocyclyl group as defined herein. Sulfonamido groups therefore include but are not limited to sulfamoyl groups (—SO$_2$NH$_2$).

The term "thiol" refers to —SH groups, while sulfides include —SR$^{40}$ groups, sulfoxides include —S(O)R$^{41}$, sulfones include —SO$_2$R$^{42}$ groups, and sulfonyls include —SO$_2$OR$^{43}$. R$^{40}$, R$^{41}$, R$^{42}$, and R$^{43}$ are each independently a substituted or unsubstituted alkyl, cycloalkyl, alkenyl, alkynyl, aryl aralkyl, heterocyclyl or heterocyclylalkyl group as defined herein.

The term "urea" refers to —NR$^{44}$—C(O)—NR$^{45}$R$^{46}$ groups. R$^{44}$, R$^{45}$, and R$^{46}$ groups are independently hydrogen, or a substituted or unsubstituted alkyl, alkenyl, alkynyl, cycloalkyl, aryl, aralkyl, heterocyclyl, or heterocyclylalkyl group as defined herein.

The term "amidine" refers to —C(NR$^{47}$)NR$^{48}$R$^{49}$ and —NR$^{47}$C(NR$^{48}$)R$^{49}$ groups, wherein R$^{47}$, R$^{48}$, and R$^{49}$ are each independently hydrogen, or a substituted or unsubstituted alkyl, cycloalkyl, alkenyl, alkynyl, aryl aralkyl, heterocyclyl or heterocyclylalkyl group as defined herein.

The term "guanidine" refers to —NR$^{50}$OC(NR$^{51}$)NR$^{52}$R$^{53}$ groups, wherein R$^{50}$, R$^{51}$, R$^{52}$ and R$^{53}$ are each independently hydrogen, or a substituted or unsubstituted alkyl, cycloalkyl, alkenyl, alkynyl, aryl aralkyl, heterocyclyl or heterocyclylalkyl group as defined herein.

The term "enamine" refers to —C(R$^{54}$)=C(R$^{55}$)NR$^{56}$R$^{57}$ and —NR$^{54}$C(R$^{55}$)=C(R$^{56}$)R$^{57}$ groups, wherein R$^{54}$, R$^{55}$, R$^{56}$ and R$^{57}$ are each independently hydrogen, a substituted or unsubstituted alkyl, cycloalkyl, alkenyl, alkynyl, aryl aralkyl, heterocyclyl or heterocyclylalkyl group as defined herein.

The term "imide" refers to —C(O)NR$^{58}$C(O)R$^{59}$ groups, wherein R$^{58}$ and R$^{59}$ are each independently hydrogen, or a substituted or unsubstituted alkyl, cycloalkyl, alkenyl, alkynyl, aryl aralkyl, heterocyclyl or heterocyclylalkyl group as defined herein.

The term "imine" refers to —CR$^{60}$(NR$^{61}$) and —N(CR$^{60}$R$^{61}$) groups, wherein R$^{60}$ and R$^{61}$ are each independently hydrogen, or a substituted or unsubstituted alkyl, cycloalkyl, alkenyl, alkynyl, aryl aralkyl, heterocyclyl or heterocyclylalkyl group as defined herein, with the proviso that not both R$^{60}$ and R$^{61}$ are simultaneously hydrogen.

Other terms may refer to combinations of specific groups encompassed by the above definitions. The following terms, while not intended to be limiting, may be used to describe certain combinations of groups. Alkanoyl refers to straight or branched chain alkylcarbonyl groups. Aroyl refers to arylcarbonyl groups. Haloalkyl refers to an alkyl having one or more halogen substituents where halogens are selected from fluorine, chlorine, bromine, or iodine. Haloalkanoyl refers to an alkanoyl group substituted with one or more halogens. Hydroxyalkyl refers to an alkyl group substituted with one or more hydroxyl (OH) groups. Hydroxyalkenyl refers to an alkenyl group substituted with one or more hydroxyl groups.

Thioalkyl refers to an alkyl substituted with one or more thiol groups. Alkoxyalkenyl refers to an alkenyl group substituted with one or more alkyl ether groups. Alkoxyalkyl refers to an alkyl having at least one ether group, alkoxyalkoxyalkyl refers to an alkoxyalkyl group substituted with an alkoxy group, and thus having two or more ether groups, and oxaalkyl generally refers to groups such as alkoxyalkyl, alkoxyalkoxyalkyl, alkoxyalkoxyalkyl, and the like. Hydroxyalkylalkoxyalkyl refers to an alkoxyalkyl group substituted with at least one hydroxyalkyl group. Heterocyclylalkyl refers to an alkyl group where one or more hydrogen atoms are replaced by a substituted or unsubstituted heterocyclyl group. Cycloalkylalkyl refers to an alkyl group substituted with a cycloalkyl group. Other combinations of individual groups will be readily apparent to one of skill in the art.

Also included are tautomers. Non-limiting examples of tautomers are keto/enol tautomers, imino/amino tautomers, N-substituted imino/N-substituted amino tautomers, thiol/thiocarbonyl tautomers, and ring-chain tautomers such as the five and six membered ring oxygen, nitrogen, sulfur, or oxygen- and sulfur-containing heterocycles also containing substituents alpha to the heteroatoms. Also specifically included are enantiomers and diastereomers, as well as racemates and isomeric mixtures of the compounds discussed herein.

In one aspect, novel compounds of DNJ are provided. In one embodiment, a compound of Formula I is provided:

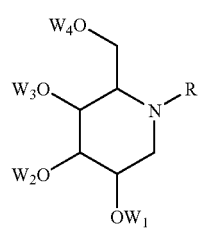

I wherein R is:

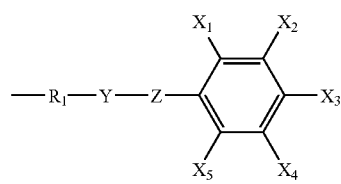

$R_1$ is a substituted or unsubstituted alkyl group;
$W_{1-4}$ are independently selected from hydrogen, substituted or unsubstituted alkyl groups, substituted or unsubstituted haloalkyl groups, substituted or unsubstituted alkanoyl groups, substituted or unsubstituted aroyl groups, or substituted or unsubstituted haloalkanoyl groups;
$X_{1-5}$ are independently selected from H, $NO_2$, $N_3$, or $NH_2$;
Y is absent or is a substituted or unsubstituted $C_1$-alkyl group other than carbonyl; and
Z is selected from a bond or NH;
provided that when Z is a bond, Y is absent, and provided that when Z is NH, Y is a substituted or unsubstituted $C_1$-alkyl group other than carbonyl.

In some embodiments, $R_1$ is an unsubstituted or substituted alkyl group having from 1 to 8 carbon atoms. In other embodiments, Z is NH. In yet other embodiments, $X_1$ and $X_3$ are $NO_2$, and $X_2$, $X_4$, and $X_5$ are H. In yet further embodiments, $X_1$ is $NO_2$, $X_3$ is $N_3$, and $X_2$, $X_4$, and $X_5$ are H. In yet other embodiments, $W_{1-4}$ are all hydrogen, and in further embodiments, Y is $CH_2$.

In some embodiments, the compound of Formula I has the structure of a compound of Formula IA:

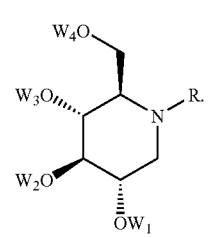

IA

In some such embodiments, the compound of Formula IA is N—(N'-{4'azido-2'-nitrophenyl)-6-aminohexyl)-deoxynojirimycin. In other such embodiments, the compound of Formula IA is N—(N'-{2',4'-dinitrophenyl)-6-aminohexyl)-deoxynojirimycin.

In another aspect, compositions of the compound of Formula I are also provided. Such compositions comprise a pharmaceutically acceptable carrier.

In another aspect, novel compounds of D-arabinitol are provided. In one embodiment, a compound of Formula II is provided:

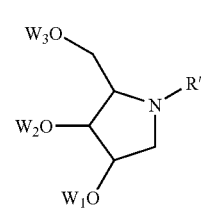

II wherein R' is:

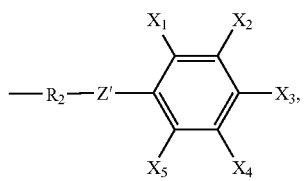

$R_2$ is a substituted or unsubstituted alkyl group;
$W_{1-3}$ are independently selected from hydrogen, substituted or unsubstituted alkyl groups, substituted or unsubstituted haloalkyl groups, substituted or unsubstituted alkanoyl groups, substituted or unsubstituted aroyl groups, or substituted or unsubstituted haloalkanoyl groups;
$X_{1-5}$ are independently selected from H, $NO_2$, $N_3$, or $NH_2$; and
Z' is selected from a bond or NH.

In some embodiments, $R_2$ is a substituted or unsubstituted alkyl group having from 1 to 8 carbon atoms. In other embodiments, Z' is NH. In yet other embodiments, $X_1$ and $X_3$ are $NO_2$, and $X_2$, $X_4$, and $X_5$ are H. In yet further embodiments, $X_1$ is $NO_2$, $X_3$ is $N_3$, and $X_2$, $X_4$, and $X_5$ are H. In yet further embodiments, $W_{1-3}$ are all hydrogen.

In some embodiments, the compound of Formula II has the structure of a compound of Formula IIA:

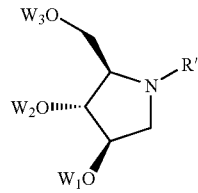

IIA

For example, compounds of Formula IIA include compounds in which $R_2$ is —$(CH_2)_6$—; $W_{1-3}$ are H; $X_1$ is $NO_2$; $X_3$ is $N_3$; $X_2$, $X_4$, and $X_5$ are H; and Z' is NH, and compounds in which $R_2$ is —$(CH_2)_6$—; $W_{1-3}$ are H; $X_1$ and $X_3$ are $NO_2$; $X_2$, $X_4$, and $X_5$ are H; and Z' is NH.

In another aspect, compositions of the compound of Formula II are also provided. Such compositions comprise a pharmaceutically acceptable carrier.

In another aspect, methods are provided for preparing analogs of DNJ and D-arabinitol. Thus in some embodiments, a method is provided comprising: preparing a compound of Formula III

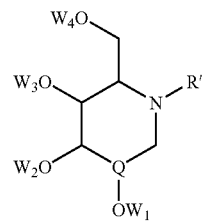

III by condensing a compound of Formula IV:

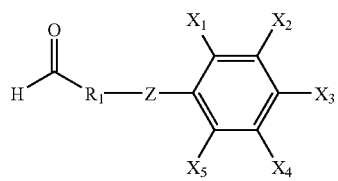

IV with a compound of Formula V

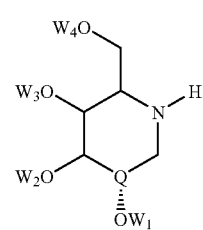

V wherein, R' is:

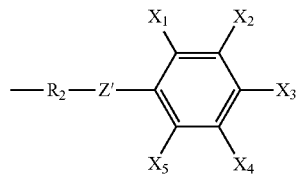

$R_2$ is a substituted or unsubstituted alkyl group;
$W_{1-4}$ are independently selected from hydrogen, substituted or unsubstituted alkyl groups, substituted or unsubstituted haloalkyl groups, substituted or unsubstituted alkanoyl groups, substituted or unsubstituted aroyl groups, or substituted or unsubstituted haloalkanoyl groups;
$X_{1-5}$ are independently selected from H, $NO_2$, $N_3$, or $NH_2$;
Z' is selected from a bond or NH; and
Q is absent or is CH,
provided that if Q is absent $OW_1$ is also absent.

In some embodiments of the methods, the condensation is by reductive amination of the compound of Formula VI with the compound of Formula V.

In other embodiments, the compound of Formula IV is prepared by aromatic fluorine displacement of a compound of Formula VI with HO—$R_2$—$NH_2$,

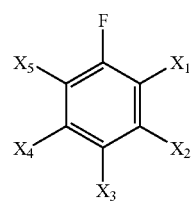

VI to form a compound of Formula VII,

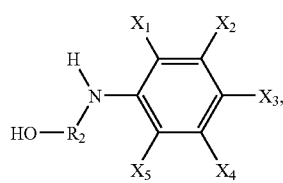

VII and oxidation of the compound of Formula VII to provide the compound of Formula IV.

In other embodiments, the compound of Formula IV is prepared by reduction of a compound of Formula VIII

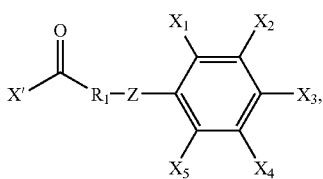

VIII where X' is selected from Cl or Br. Compounds of Formula VIII may be prepared from commercially available precursor compounds by methods known to those of skill in the art. As a non-limiting example, 4-phenylbutyric acid may be converted to 2,4-dinitrophenylbutyric acid, followed by reduction of the 4-nitro group to an amine, and conversion to 2-nitro-4-azidophenylbutyric acid. The corresponding aldehyde, i.e. a compound of Formula IV, is then prepared by conversion of the 2-nitro-4-azidophenylbutyric acid into the corresponding acid chloride, followed by reduction to the aldehyde according to methods well known in the art.

In some embodiments, the compound of Formula III has the structure of a compound of Formula IIIA.

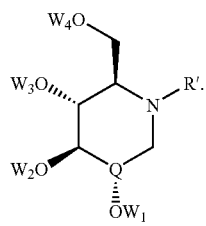

IIIA

As described above, DNJ, D-arabinitol and certain N-alkylated modifications thereof are potent α-glucosidase inhibitors. Thus in another aspect of the invention, methods are provided for inhibiting α-glucosidase with the compounds of Formula I and II. In some embodiments, the methods include inhibiting an α-glucosidase with a compound of Formula I or a salt thereof, a compound of Formula II or a salt thereof, or a mixture of any two or more thereof:

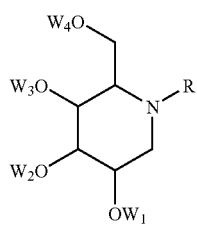

I

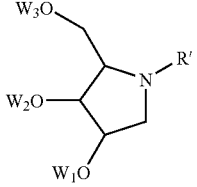

II wherein R is:

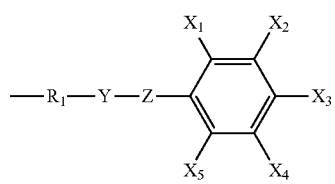

R' is:

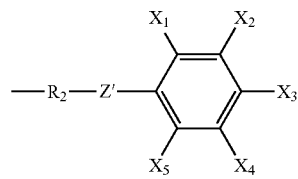

$R_1$ is a substituted or unsubstituted alkyl group;
$R_2$ is a substituted or unsubstituted alkyl group,
$W_{1-4}$ are independently selected from hydrogen, substituted or unsubstituted alkyl groups, substituted or unsubstituted haloalkyl groups, substituted or unsubstituted alkanoyl groups, substituted or unsubstituted aroyl groups, or substituted or unsubstituted haloalkanoyl groups;
$X_{1-5}$ are independently selected from H, $NO_2$, $N_3$, or $NH_2$;
Y is absent or is a substituted or unsubstituted $C_1$-alkyl group other than carbonyl;
Z is selected from a bond or NH;
  provided that when Z is a bond, Y is absent, and
  provided that when Z is NH, Y is a substituted or unsubstituted $C_1$-alkyl group, other than carbonyl; and
Z' is a bond or NH.

In some embodiments of the methods, $R_1$ or $R_2$ have from 1 to 8 carbon atoms. In other embodiments, $X_1$ and $X_3$ are $NO_2$, and $X_2$, $X_4$, and $X_5$ are H. In yet other embodiments, $X_1$ is $NO_2$, $X_3$ is $N_3$, and $X_2$, $X_4$, and $X_5$ are H. In yet further embodiments, Y is $CH_2$.

In some embodiments of the methods, the α-glucosidase is selected from α-glucosidase I or α-glucosidase II.

In some such embodiments, the salt of the compound is a pharmaceutically acceptable salt. In some embodiments, the salt is an alkali metal salt, an alkaline earth metal salt, or a mixture of any two or more thereof. In other embodiments, the salt is selected from sodium, potassium, calcium, magnesium salts, organic base or basic quaternary ammonium salts, and the like or mixtures of any two or more thereof.

In other embodiments, the compound of Formula I has the structure of a compound of Formula IA, and/or the compound of Formula II has the structure of compound of Formula IIA:

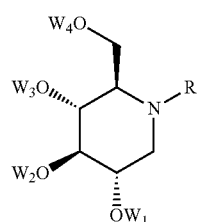

IA

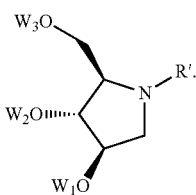

IIA

In some embodiments, the methods of inhibiting α-glucosidase further comprise photolyzing the compound in the presence of the α-glucosidase. In certain embodiments, the α-glucosidase may be inhibited in the presence of a labeled substrate. For example, compounds described herein and those analogs having a radiolabel, such as a $^{14}$C label (H. R. Mellor et al., *Preparation, Biochemical Characterisation and Biological Properties of Radiolabelled N-alkylated Deoxynojirimycins,* 336 *Biochem. J.* 225-233 (2002)), may bind selectively to α-glucosidases in a cell, and may then be activated by irradiation to form a highly reactive species which may covalently insert into amino acid residues at the active site(s) of the α-glucosidases. This may be accomplished in the example of an azide compound where the azide compound is photoactivated to produce a nitrene that then reacts with the amino acid forming a hydrazide compound, as illustrated in Scheme I. When electron withdrawing groups are present on the aromatic ring (Ar), the aryl nitrene is more reactive toward nucleophiles, than toward another aryl nitrene. Thus, when labeling proteins which contain amino acids ($R_{AA}$) having nucleophilic groups (the ε-amino group in lysine for example), intermolecular reactions are favored over competing intramolecular reactions.

Scheme I. Formation of nitrenes from azides and covalent labelling of amino groups in a biomolecule.

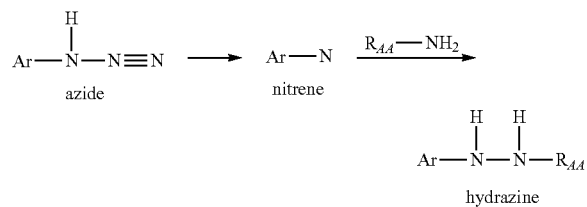

In another aspect of the invention, a method is provided comprising: inhibiting removal of glucose residues from an oligosaccharide by contacting an α-glucosidase with a compound of Formula I or a salt thereof, a compound of Formula II or a salt thereof, or a mixture of any two or more thereof:

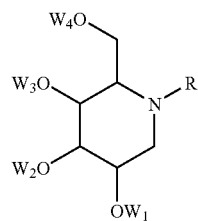

I

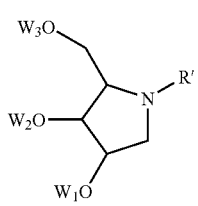

II wherein R is:

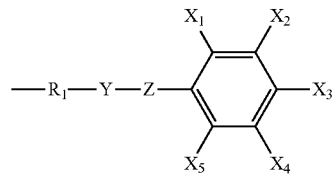

R' is:

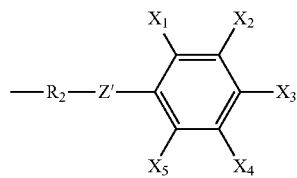

$R_1$ is a substituted or unsubstituted alkyl group;

$R_2$ is a substituted or unsubstituted alkyl group;

$W_{1-4}$ are independently selected from hydrogen, substituted or unsubstituted alkyl groups, substituted or unsubstituted haloalkyl groups, substituted or unsubstituted alkanoyl groups, substituted or unsubstituted aroyl groups, or substituted or unsubstituted haloalkanoyl groups;

$X_{1-5}$ are independently selected from H, $NO_2$, $N_3$, or $NH_2$;

Y is absent or is a substituted or unsubstituted $C_1$-alkyl group other than carbonyl;

Z is selected from a bond or NH;

provided that when Z is a bond, Y is absent, and provided that when Z is NH, Y is a substituted or unsubstituted $C_1$-alkyl group, other than carbonyl; and Z' is a bond or NH.

N-alkylated modifications of DNJ and D-arabinitol, such as N-butyl-DNJ may be used as antiviral agents. Thus, in another aspect of the invention, methods are provided for inhibiting a virus infecting a mammal comprising contacting a mammalian cell infected with a virus, with a compound of Formula I or a pharmaceutically acceptable salt thereof, a compound of Formula II or a pharmaceutically acceptable salt thereof, or a mixture of any two or more thereof, in an amount effective to inhibit the virus:

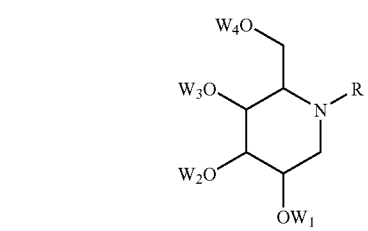

I

-continued

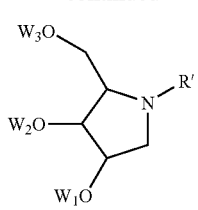

wherein R is:

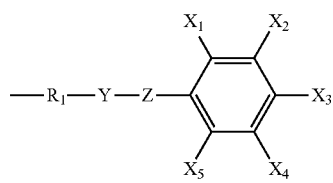

R' is:

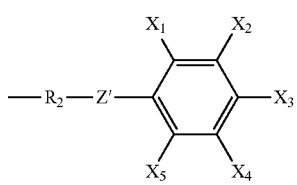

R₁ is a substituted or unsubstituted alkyl group;
R₂ is a substituted or unsubstituted alkyl group,
$W_{1-4}$ are independently selected from hydrogen, substituted or unsubstituted alkyl groups, substituted or unsubstituted haloalkyl groups, substituted or unsubstituted alkanoyl groups, substituted or unsubstituted aroyl groups, or substituted or unsubstituted haloalkanoyl groups;
$X_{1-5}$ are independently selected from H, $NO_2$, $N_3$, or $NH_2$;
Y is absent or is a substituted or unsubstituted $C_1$-alkyl group other than carbonyl;
Z is selected from a bond or NH;
provided that when Z is a bond, Y is absent, and
provided that when Z is NH, Y is a substituted or unsubstituted $C_1$-alkyl group, other than carbonyl; and
Z' is a bond or NH.

In some embodiments, the virus is the virus belongs to the Flaviviridae family of viruses. The virus may be selected from, but is not limited to a hepatitis virus such as hepatitis B virus or hepatitis C virus, or bovine viral diarrhea virus. In such embodiments, the amount effective to inhibit the virus, is an amount effective to inhibit a hepatitis virus, a hepatitis B virus, a hepatitis C virus, or a bovine diarrhea virus. In another embodiment, the compounds of Formula I and II, may be contacted alone or in combination with nucleotide antiviral compounds, nucleoside antiviral compounds, immunostimulating compounds, immunomodulating compounds, or a mixture of any two or more thereof, known to those of skill in the art. In some embodiments, the contacting further comprises administering the compound of Formula I or II to a mammal. In some embodiments, the mammalian cell is a human cell. In yet other embodiments, the contacting comprises administering the compound of Formula I or II to a human.

For the purposes of this disclosure and unless otherwise specified, "a" or "an" means "one or more."

One skilled in the art will readily realize that all ranges discussed can and do necessarily also describe all subranges therein for all purposes and that all such subranges also form part and parcel of this invention. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present invention, thus generally described, will be understood more readily by reference to the following examples, which are provided by way of illustration and are not intended to be limiting of the present invention.

Example 1

Synthesis of N—(N'-{4'azido-2'-nitrophenyl)-6-aminohexyl)-DNJ (NAP-DNJ)

Direct displacement of the aromatic fluorine in 4-fluor-3-nitrophenyl azide (FNAP) by 6-aminohexanol produces the desired alcohol which is oxidized to the aldehyde. The resulting aldehyde is subjected to reductive amination with DNJ to produce the final product as shown in Scheme II.

Scheme II.

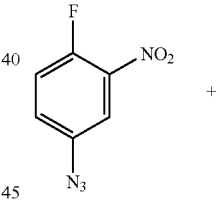

+

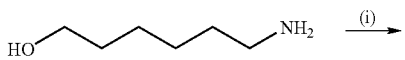

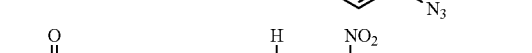

-continued

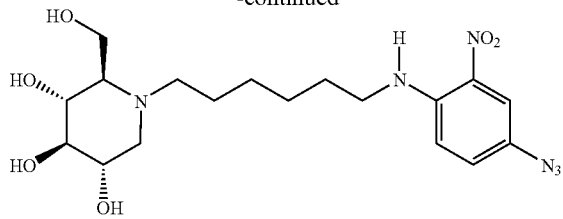

(i) triethylamine (2.2 equiv.), 1,4-dioxane, rt, 2 h, 55%; (ii) Dess-Martin (1.2 equiv.), DCM, rt, 2 h, 95%; and (iii) DNJ, NaCNBH3 (1.5 equiv.), AcOH, MeOH, rt, 14 h, quantitative yield.

Characterization of the NAP-DNJ was conducted using $^1$H and $^{13}$C NMR and mass spectrometry. The results from 1D ($^1$H and $^{13}$C) NMR are tabulated in Table 1, and the COSY and NOESY results are shown below. $^1$H NMR are arbitrary and $^{13}$C NMR are referenced to methanol (49.0 ppm).

TABLE 1

| Atom | $^1$H NMR (500 mHz) | | | $^{13}$C NMR | | |
|---|---|---|---|---|---|---|
| | δ (ppm) | mult | $^3J_{HH}$ (Hz) | δ (ppm) | mult | $^1J_{CH}$ (Hz) |
| C1 | 2.878 | dd | 11.2/4.9 | 57.7 | | |
| | 2.054 | dd | 11.2/10.4 | | | |
| C2 | 3.352 | ddd | 4.9/10.4/9.2 | 70.8 | | |
| C3 | 3.013 | dd | 9.2/9.1 | 80.6 | | |
| C4 | 3.227 | dd | 9.1/9.6 | 72.1 | | |
| C5 | 2.004 | ddd | 9.6/2.7/2.7 | 67.5 | | |
| C6 | 3.753 | dd | 11.9/2.7 | 59.6 | | |
| | 3.711 | dd | 11.9/2.7 | | | |
| C7 | 2.703 | ddd | | 53.7 | | |
| | 2.461 | ddd | | | | |
| C8 | 1.42 | o/i | | 25.3 | | |
| C9 | 1.260 | m | | 28.2 | | |
| C10 | 1.38 | o/i | | 27.9 | | |
| C11 | 1.615 | m | | 30.0 | | |
| C12 | 3.258 | t | | 43.9 | | |
| C13 | — | — | | 128.8 | | |
| C14 | — | — | | 132.5 | | |
| C15 | 7.668 | d | 2.7 | 116.5 | | |
| C16 | — | — | | 144.7 | | |
| C17 | 7.137 | dd | 2.7/9.2 | 129.3 | | |
| C18 | 6.965 | d | 9.2 | 117.3 | | |

$^1$H-$^1$H COSY experiment: C1H/H'—C2H—C3H—C4H—C5H—C6H/H'; C7H/H'—C8H$_2$—C9H$_2$—C10H$_2$—C11H$_2$—C12H$_2$; C15H—C17H—C18H. The aromatic ring is therefore 1,2,4-substituted and the C7 is attached, or part of a rigid ring.

NOESY experiment (400 msec): C7H→C1H (138), C6H/H' (343); C7H'→C6H/H' (325); C12H$_2$→C18H. The large coupling constants around the ring suggest that C1H', C2H, C3H, C4H and C5H are all trans di-axial. This indicates that the ring has glucose stereochemistry, i.e., is DNJ. The NOES from C7H/H' to C1H/H' and C6H/H' indicates that C12 is linked to the aromatic ring and probably in a ring position ortho to C18.

Spectroscopy: $[\alpha]_D^{22}$ –7.7 (c 0.026, MeOH); $\nu_{max}$ (Ge) 3356 (NH+OH), 2926, 2856 (CH), 2119 (N$_3$), 1633, 1556 (C=C), 1521, 1347 (NO$_2$) cm$^{-1}$. Mass spectrometry: m/z (ES+): 425.33 ([M+H]$^+$, 100%); HRMS (ES+): Found 425.2152 ([M+H]+) required 426.2149.

Example 2

Synthesis of N—(N'-{2,4-dinitrophenyl)-6-aminohexyl)-DNJ (NDP-DNJ)

Direct displacement of the aromatic fluorine in 2,4-dinitrofluorobenzene (Sanger's reagent) by 6-aminohexanol produces the desired alcohol which is oxidized to the aldehyde. The resulting aldehyde is subjected to reductive amination with DNJ to produce the final product (Scheme III).

Scheme III.

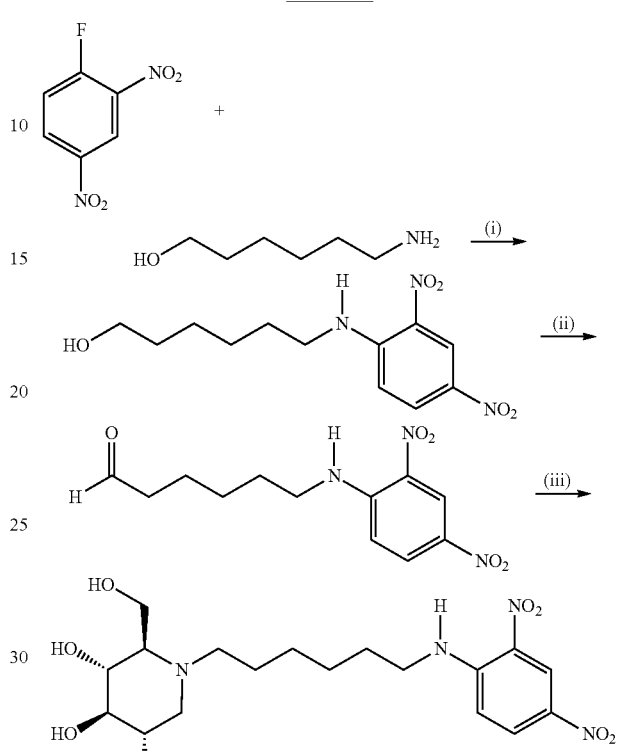

(i) triethylamine (1.1 equiv.), 1,4-dioxane, rt, 1 h, 97%; (ii) Dess-Martin (1.2 equiv.), DCM, rt, 2 h, 76%; (iii) DNJ, NaCNBH3 (1.2 equiv.), AcOH, MeOH, rt, 16 h, 52%.

Characterization of the NDP-DNJ was conducted and the results are shown below.

$\delta_H$ (500.3 MHz, MeOD): 1.33-1.58 (6H, m, H-3'ab, H-4'ab, H-2'ab), 1.77 (2H, a-quin, J 7.4 Hz, H-5'ab), 2.11 (1H, a-dt, J$_{5,4}$ 9.5 Hz, J 2.8 Hz, H-5), 2.16 (1H, a-t, J 10.8 Hz, H-1a), 2.54-2.61 (1H, m, H-1'a), 2.79-2.85 (1H, m, H-1'b), 2.98 (1H, dd, J$_{1b,1a}$ 11.2 Hz, J$_{1b,2}$ 4.9 Hz, H-1b), 3.12 (1H, a-t, J 9.1 Hz, H-3), 3.33 (1H, a-t, J 9.3 Hz, H-4), 3.46 (1H, ddd, J$_{2,1a}$ 10.4 Hz, J$_{2,3}$ 9.2 Hz, J$_{2,1b}$ 4.9 Hz, H-2), 3.50 (2H, a-t, J 7.2 Hz, H-6'), 3.82 (1H, dd, J$_{6a,6b}$ 11.9 Hz, J$_{6a,5}$ 2.9 Hz, H-6a), 3.86 (1H, dd, J$_{6b,6a}$ 11.9 Hz, J$_{6b,5}$ 2.7 Hz, H-6b), 7.16 (1H, d, J$_{6'',5''}$ 9.6 Hz, H-6''), 8.28 (1H, dd, J$_{5'',6''}$ 9.6 Hz, J$_{5'',3''}$ 2.7 Hz, H-5''), 9.03 (1H, d, J$_{3'',5''}$ 2.7 Hz, H-3'').

$\delta_C$ (125.8 MHz, MeOD): 25.2 (C-2'), 27.9 (C-4'), 28.3 (C-3'), 29.7 (C-5'), 44.2 (C-6'), 53.7 (C-1'), 57.7 (C-1'), 59.6 (C-6), 67.5 (C-5), 70.8 (C-2), 72.1 (C-4), 80.6 (C-3), 115.8 (C-6''), 124.8 (C-3''), 131.1 (C-5''), 131.5 (C-1''), 136.9 (C-2''), 149.8 (C-4'').

Spectroscopy: $[\alpha]_D$ –7.9 (c 0.14, MeOH); $\nu_{max}$ (Ge) 3356 (OH+NH), 1572, 1339 (NO$_2$) cm$^{-1}$. Mass spectrometry: m/z HRMS (ESI$^+$): Found 429.1973, C$_{18}$H$_{29}$N$_4$O$_8$ [M+H]$^+$ requires 429.1985.

Example 3

Synthesis of N-(alkylphenyl)-DNJ Derivatives

As shown below in Scheme IV, N-alkylphenyl-DNJ compounds can be prepared from phenylcarboxylic acids. In Scheme IV, 4-phenylbutyric acid is converted to 2,4-dinitrophenylbutyric acid, followed by reduction of the 4-nitro group to an amine, and conversion to 2-nitro-4-azidophenylbutyric acid. The aldehyde can then be prepared by conversion of the 2-nitro-4-azidophenylbutyric acid into the corresponding acid chloride, followed by reduction to the aldehyde. The resulting aldehyde can be subjected to reductive amination with DNJ to produce the final product. Alternatively, D-arabinitol may be used in place of the DNJ to produce the corresponding D-arabinitol compound.

Scheme IV. Synthesis of C-phenyl-DNJ derivatives.

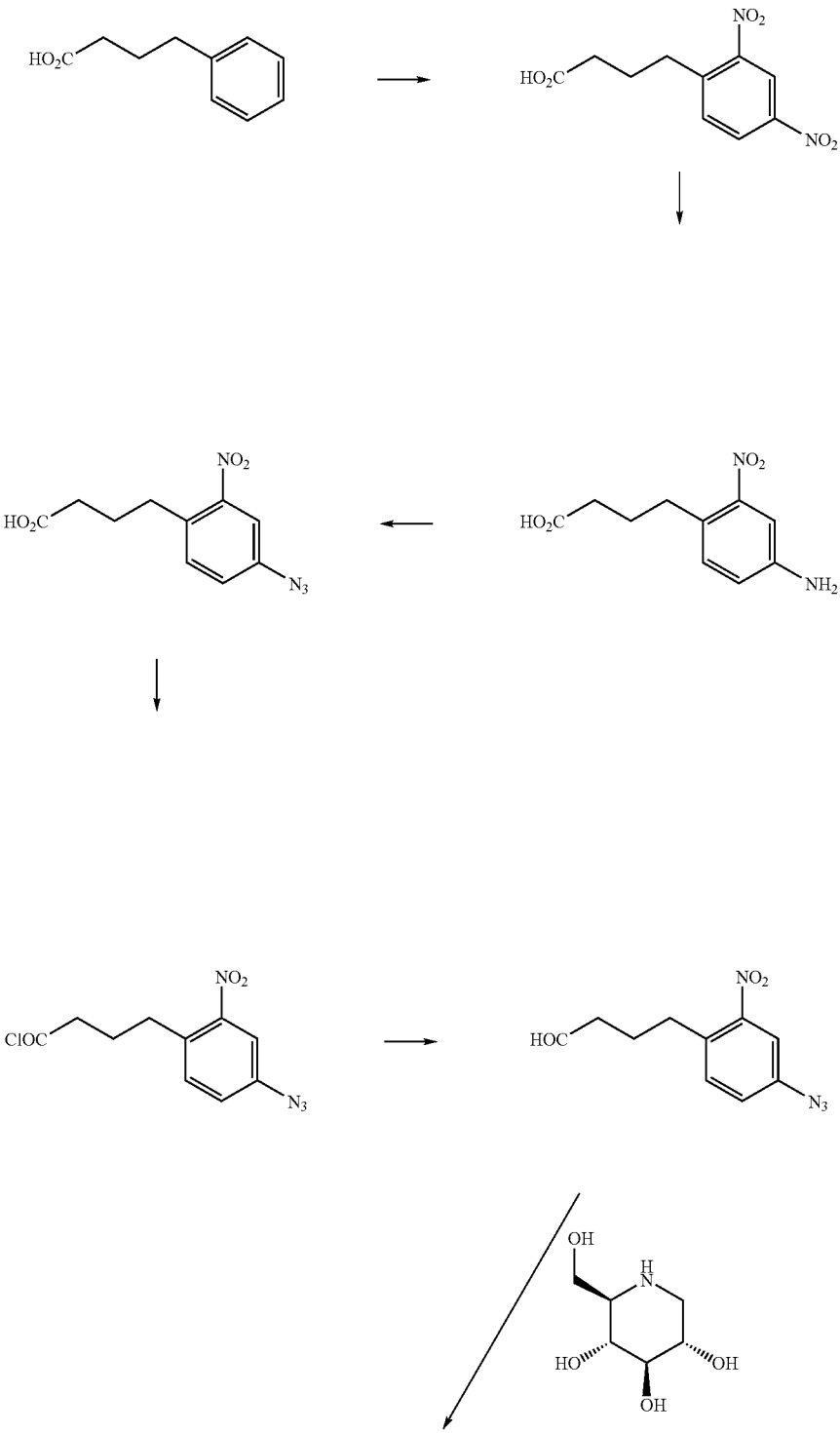

-continued

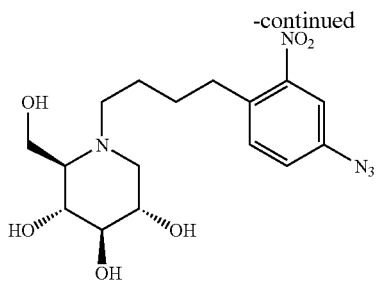

Example 4

The effect of an ER-glucosidase inhibitor on cells was evaluated using an assay method by modifying known methods. (H. R. Mellor et al., *Cellular Effects of Deoxynojirimycin Analogues: Inhibition of N-Linked Oligosaccharide Processing and Generation of Free Glucosylated Oligosaccharides,* 381 Biochem. J. 867-875 (2004). The detection of free oligosaccharides following imino sugar treatment to generate misfolded protein that is degraded in the cytosol is an accurate measure of cell ER entry and inhibition of glycoprotein processing of α-glucosidases I and II by imino sugars.

Cells were cultured to high density ($\times 10^7$ cells/ml) prior to growth in fresh medium containing NB-DNJ at varying concentrations. The cells were seeded at a lower density so as to achieve a high density at the end of the incubation period. Following cell culture, the medium was removed and the cells were washed 3 times with PBS by centrifugation. Washed cells were stored at −20° C. for a short time before thawing, and glass homogenization in water. The conditions for extraction of FOS were determined to maximize recovery of FOS. Essentially, the homogenate is desalted and deproteinated by passaging through a mixed bed ion exchange column (0.2 ml AG5OW-XI2 ($H^+$, 100-200 mesh) over 0.4 ml AG3-X4 ($OH^-$, 100-200 mesh) and pre-equilibrated with water (5×1 ml). The homogenate is added to the column, which is washed with 4×1 ml water, and the eluate collected. The extracted, purified FOS is then dried under vacuum or by freeze-drying.

FOS were labeled with anthranilic acid by methods known in the art. (D. C. Neville, et al, *Analysis of Fluorescently Labeled Glycosphingolipid-Derived Oligosaccharides Following Ceramide Glycanase Digestion and Anthranilic Acid Labeling,* 331, Anal. Biochem. 275-282 (2004).) Briefly, anthranilic acid (30 mg/ml) was dissolved in a solution of sodium acetate trihydrate (4%, w/v) and boric acid (2%, w/v) in methanol. This solution was added to solid sodium cyanoborohydride to give a final concentration of 45 mg/ml. The resulting solution was mixed to give the final labeling mixture. The dried FOS was dissolved in 30 µl water, and 80 µl of labeling mixture was added prior to incubating at 80° C. for 45-60 min. The reaction was allowed to cool to room temperature, 1 ml acetonitrile/water (97:3, v/v) was added, and the mixture vortexed. Labeled oligosaccharides were purified by chromatography through Discovery DPA-6S columns. The columns were pre-equilibrated with 2×1 ml acetonitrile. The samples were loaded using gravity flow and allowed to drip through the column. The column was washed with 4×1 ml acetonitrile/water (99:1, v/v) followed by 0.5 ml acetonitrile/water (97:3, v/v). The labeled oligosaccharides were eluted with 2×0.6 ml water.

Labeled oligosaccharides in 50 mM Tris/HCl buffer at pH 7.2, were purified using a Concanavalin A (Con A)-Sepharose 4B column (100 µl packed resin). The column was pre-equilibrated with 2×1 ml water followed by 1 ml of 1 mM $MgCl_2$, 1 mM $CaCl_2$ and 1 mM $MnCl_2$ in water, and finally 2×1 ml 50 mM Tris/HCl buffer pH 7.2. The sample was added and allowed to interact with the column for 30 minutes before being washed with 2×1 ml 50 mM Tris/HCl buffer, pH 7.2. The Con A bound, FOS were then eluted with 2×1 ml of hot (70° C.) 0.5 M methyl-α-D-mannopyranoside in 50 mM Tris/HCl buffer, pH 7.2.

ConA-Sepharose purified 2-AA-labeled oligosaccharides were separated by NP-HPLC using a 4.6×250 mm TSKgel Amide-80 column (Anachem, Luton, UK) with slight modifications to known methods. (D. C. Neville, et al.) The chromatography system consisted of a Waters Alliance 2695 separations module and an in-line Waters 474 fluorescence detector set at an excitation wavelength of 360 nm and emission wavelength of 425 nm. All chromatography was performed at 30° C. The first solvent, solvent A, was acetonitrile and the second solvent, solvent B, was Milli-Q water. Solvent C was composed of 100 mM ammonium hydroxide, titrated to pH 3.85 with acetic acid, in Milli-Q water and was prepared using a standard 5 N ammonium hydroxide solution (Sigma). Gradient conditions were as follows: time=0 min (t=0), 71.6% A, 8.4% B, 20% C (0.8 ml/min); t=6, 71.6% A, 8.4% B, 20% C (0.8 ml/min); t=40, 52% A, 28% B, 20% C (0.8 ml/min); t=41, 23% A, 57% B, 20% C (1 ml/min); t=43, 23% A, 57% B, 20% C (1 ml/min); t=44, 71.6% A, 8.4% B, 20% C (1.2 ml/min); t=59, 71.6% A, 8.4% B, 20% C (1.2 ml/min); t=60, 71.6% A, 8.4% B, 20% C (0.8 ml/min). Samples (<50 µl) were injected in Milli-Q water/acetonitrile (3/7, v/v). All chromatography was controlled, including data collection and processing, using Waters Empower software. Glucose units were determined, following comparison with a 2-AA-labeled glucose oligomer ladder (derived from a partial hydrolysate of dextran) external standard using Peak Time software (developed in-house).

Purified α-glucosidase I and II were purified from rat liver by known methods. (G. B. Karlsson, et al., *Effects of the Imino Sugar N-Butyldeoxynojirimycin on the N-Glycosylation of Recombinant gp120,* 268 J. Biol. Chem., 570-576 (1993).) Substrates were prepared from the isolation of FOS generated from cells treated with NB-DNJ, as a glucosidase inhibitor, and purified by HPLC. 2-AA-labeled FOS were isolated and purified as substrates for either α-glucosidase I or II. Fluorescently-labeled substrates $Glc_1Man_5GlcNAc_1$ (G1M5N), $Glc_2Man_5GlcNAc_1$ (G2M5N), $Glc_3Man_5GlcNAc_1$ (G3M5N) and $Glc_3Man_9GlcNAc_1$ (G3M9N2) were added to separate 1.5 ml centrifuge tubes with varying concentrations of imino sugar and dried under vacuum. Sufficient α-glucosidase I was added to generate 25% hydrolysis of G3M5N in a 30 minute reaction time. Similarly, α-glucosidase II was incubated for 2 hours with G2M5N and 20 minutes with G1M5N. In all cases, linear degradation of substrate occurred over the time of incubation. The reactions were stopped by the addition of 30 µl acetonitrile. Following enzyme treatment, all digests were centrifuged through a 10,000 molecular weight cut off filter at 7,000 rpm for 45 minutes (which had been pre-washed with 150 µl of water) to remove protein before HPLC analysis, as described above, and analyzed by HPLC as above.

Results of Examples 1-3

In Vitro Inhibition of α-Glucosidases I and II $IC_{50}$ values were generated using a range of inhibitors concentrations for α-glucosidase I and α-glucosidase II substrates, labeled with 2-AA as shown below. The inhibition by N-butyl-DNJ (NB-DNJ) is shown in comparison.

Pentamannose Substrates

Manα6
         ╲
          Manβ4GlcNAc-2AA
Glcα2Glcα3Glcα3Manα2Manα2Manα3 ╱
         a      b
Glucosidase 1   Glucosidase II

| Enzyme Substrate | α-Glucosidase I $Glc_3Man_5GlcNAc_1$ $IC_{50}$ (μM) | α-Glucosidase II (a) $Glc_2Man_5GlcNAc_1$ $IC_{50}$ (μM) | α-Glucosidase II (b) $Glc_1Man_5GlcNAc_1$ $IC_{50}$ (μM) |
|---|---|---|---|
| NAP-DNJ | 0.017 ± 0.001 | 0.30 ± 0.1 | 0.833 ± 0.18 |
| NDP-DNJ | 0.108 ± 0.02 | 6.9 ± 3.4 | 1.9 ± 0.4 |
| NB-DNJ | 0.68 ± 0.15 | 10.8 ± 1.1 | 53.0 ± 16.6 |

These data reveal that the inhibition by NAP-DNJ was 20 and 50 times better for α-glucosidase I than α-glucosidase II (a) or (b) activities respectively. Inhibition of α-glucosidase I improved 40-fold in comparison to NB-DNJ. However, these structures are only seen as FOS by the cell and more physiologically relevant ER-localized substrates were analyzed.

Heptamannose substrates

Manα6
     ╲
      Manα6
Manα3 ╱    ╲
            Manβ4GlcNAc-2AA
Glcα2Glcα3Glcα3Manα2Manα2Manα3 ╱
         a      b
Glucosidase 1   Glucosidase II

| Enzyme Substrate | α-Glucosidase I $Glc_3Man_7GlcNAc_1$ $IC_{50}$ (μM) | α-Glucosidase II (a) $Glc_2Man_7GlcNAc_1$ $IC_{50}$ (μM) | α-Glucosidase II (b) $Glc_1Man_7GlcNAc_1$ $IC_{50}$ (μM) |
|---|---|---|---|
| NAP-DNJ | 0.037 ± 0.001 | 11.7 ± 0.7 | 19.2 ± 0.06 |
| NDP-DNJ | 0.045 ± 0.003 | 18.1 ± 1.6 | 10.2 ± 0.02 |
| NB-DNJ | nd | nd | nd | nd = Not determined

These data reveal that substrates with mannose structures more similar to those found physiologically show marked discrimination to glucosidase inhibition. NAP-DNJ is over 300 times more potent in inhibiting glucosidase I than glucosidase II (a) and more than 500 times than glucosidase II (b). Similar improvements were also observed with NDP-DNJ. A final in vitro experiment was performed with the oligosaccharide substrate usually modified by glucosidases in the ER.

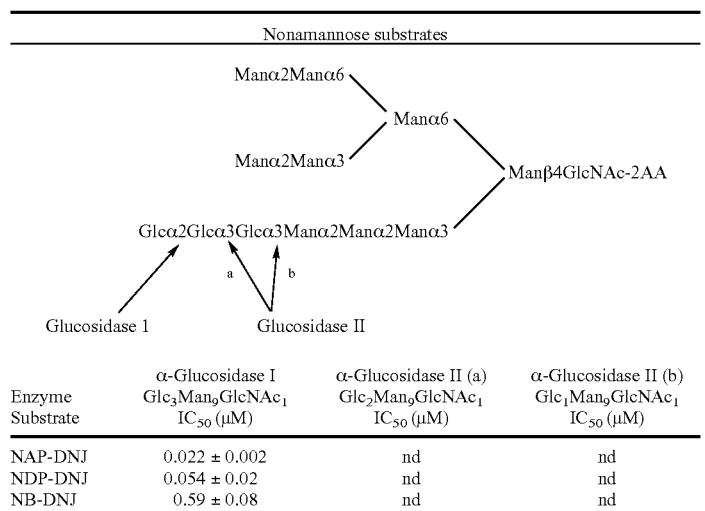

| | α-Glucosidase I | α-Glucosidase II (a) | α-Glucosidase II (b) |
| Enzyme | Glc₃Man₉GlcNAc₁ | Glc₂Man₉GlcNAc₁ | Glc₁Man₉GlcNAc₁ |
| Substrate | IC$_{50}$ (µM) | IC$_{50}$ (µM) | IC$_{50}$ (µM) |
|---|---|---|---|
| NAP-DNJ | 0.022 ± 0.002 | nd | nd |
| NDP-DNJ | 0.054 ± 0.02 | nd | nd |
| NB-DNJ | 0.59 ± 0.08 | nd | nd | nd = Not determined

These data reveal that the IC$_{50}$ values for inhibitors may not be dependent on the mannose architecture for glucosidase I mediated hydrolysis of tri-glucosylated substrates, but glucosidase II may be dependent. This may indicate that using physiologically relevant substrates, NAP-DNJ is 25-50 times better than NB-DNJ in inhibiting all triglucosylated structures and 300-500 times better at inhibiting glucosidase I than glucosidase II (a) and (b) activity.

Inhibition of Glucosidase Activity in Cells

HL60 cells were incubated with various concentrations of NAP-DNJ, DNP-DNJ and NB-DNJ (as an inhibitor reference) for 24 h and the free oligosaccharides isolated, labeled and characterized by NP-HPLC (FIG. 1). FIG. 1 depicts NP-HPLC results for FOS isolated from control cells (a); NAP-DNJ (50 µM) treated cells (b); DNP-DNJ (50 µM) treated cells (c), and NB-DNJ (1 mM) treated cells (d). Peaks were assigned by reference to known, purified standards whose structures were characterized by mass spectrometry and digestion using purified glucosidases and mannosidases.

Figure 2:
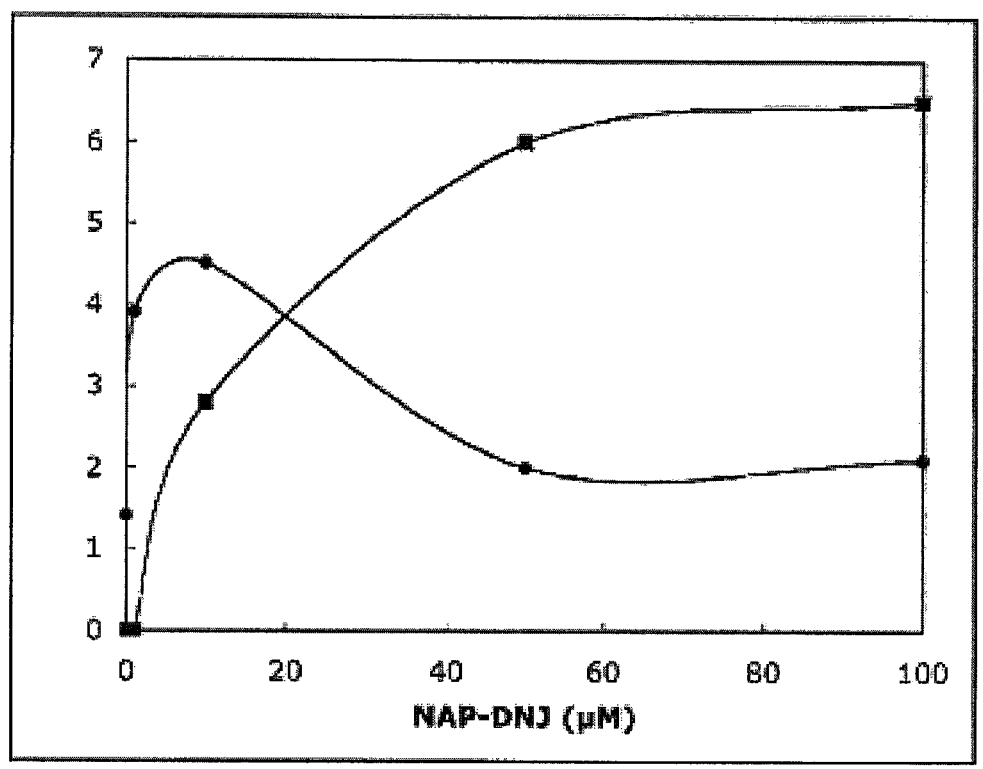
FIG. 2 is a graph following treatment of HL60 cells for 24 h with various concentrations of NAP-DNJ, free oligosaccharides were isolated and separated by NP-HPLC.

These data reveal that in cells, NAP-DNJ is considerably more potent (20-50 times) at inhibiting glucosidase I (estimation of the product of glucosidase I inhibition, G3M5N) than NB-DNJ. The effect of NAP-DNJ concentration on the relative inhibition of glucosidase I and II is seen in FIG. 2. FIG. 2 is a graph following treatment of HL60 cells for 24 h with various concentrations of NAP-DNJ, free oligosaccharides were isolated and separated by NP-HPLC. Peak areas corresponding to inhibition of glucosidase I (G3M5N) and glucosidase II (b) (G1M5N) were measured and normalized to the amount of M4, a free oligosaccharide unaffected by glucosidase inhibition used as an internal marker. Normalization to protein amounts gave the same result.

These data show the relative efficacy of NAP-DNJ for glucosidases. Despite the apparent weaker potency for glucosidase II using in vitro assays, NAP-DNJ inhibits the enzyme in cells at very low concentrations (1-10 µM). Glucosidase I is inhibited with increasing amounts of NAP-DNJ, to a maximal amount at 50-100 ρM, reducing the available substrate for glucosidase II, which decreases in the amounts observed (FIG. 2).

While some embodiments have been illustrated and described, it should be understood that changes and modifications can be made therein in accordance with ordinary skill in the art without departing from the invention in its broader aspects as defined in the following claims.

We claim:
1. A compound of Formula I:

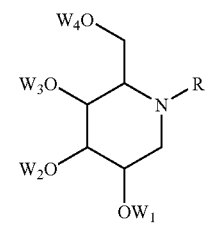

wherein R is:

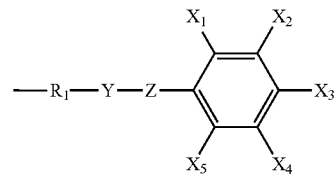

$R_1$ is a substituted or unsubstituted butyl, pentyl, hexyl, heptyl, or octyl group;

$W_{1-4}$ are independently selected from hydrogen, substituted or unsubstituted alkyl groups, substituted or unsubstituted haloalkyl groups, substituted or unsubstituted alkanoyl groups, substituted or unsubstituted aroyl groups, or substituted or unsubstituted haloalkanoyl groups;

$X_1$ is $NO_2$; $X_3$ is $NO_2$ or $N_3$; $X_2$, $X_4$ and $X_5$ are each H;

Y is a substituted or unsubstituted $C_1$-alkyl group, other than carbonyl; and

Z is NH.

2. The compound of claim 1, wherein $X_3$ is $NO_2$.

3. The compound of claim 1, wherein $X_3$ is $N_3$.

4. The compound of claim 1, wherein $W_{1-4}$ are H.

5. The compound of claim 1, wherein Y is $CH_2$.

6. The compound of claim 1, wherein the compound of Formula I has the structure of the compound of Formula IA:

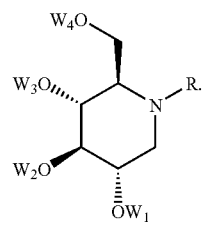

IA

7. The compound of claim 6, wherein
$R_1$ is —$(CH_2)_5$—;
$W_{1-4}$ are H;
$X_1$ is $NO_2$;
$X_3$ is $N_3$;
$X_2$, $X_4$, and $X_5$ are H;
Y is —$(CH_2)$—; and
Z is NH.

8. The compound of claim 6, wherein
$R_1$ is —$(CH_2)_5$—;
$W_{1-4}$ are H;
$X_1$ and $X_3$ are $NO_2$;
$X_2$, $X_4$, and $X_5$ are H;
Y is —$(CH_2)$—; and
Z is NH.

9. A composition comprising the compound of claim 1 and a pharmaceutically acceptable carrier.

10. A method for preparing a compound of Formula III

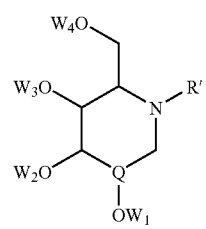

III comprising-condensing a compound of Formula IV:

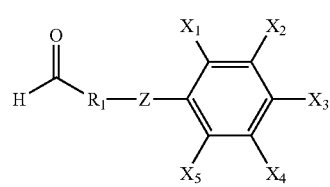

IV with a compound of Formula V

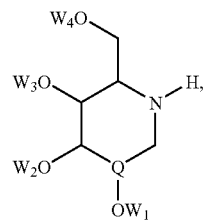

V wherein,
R' is:

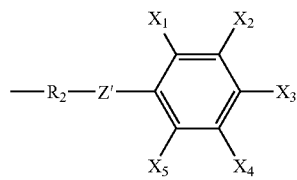

Q is CH,
$R_1$ is a substituted or unsubstituted butyl, pentyl, hexyl, heptyl, or octyl group;
$R_2$ is a substituted or unsubstituted alkyl group;
$W_{1-4}$ are independently hydrogen, substituted or unsubstituted alkyl groups, substituted or unsubstituted haloalkyl groups, substituted or unsubstituted alkanoyl groups, substituted or unsubstituted aroyl groups, or substituted or substituted haloalkanoyl groups;
$X_1$ is $NO_2$; $X_3$ is $NO_2$ or $N_3$; $X_2$, $X_4$ and $X_5$ are each H; and
Z' is NH to obtain the compound of Formula III.

11. The method of claim 10, wherein the condensation is by reductive amination of the compound of Formula VI with the compound of Formula V.

12. The method of claim 10, wherein the compound of Formula IV is prepared by aromatic fluorine displacement of a compound of Formula VI with HO—$R_2$—$NH_2$,

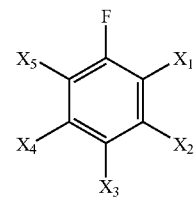

VI to form a compound of Formula VII,

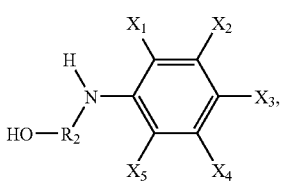

VII and oxidation of the compound of Formula VII to provide the compound of Formula IV.

13. The method of claim 10, wherein the compound of Formula III has a stereochemistry of a compound of Formula IIIA,

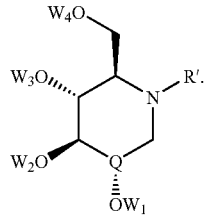

14. A method comprising:
inhibiting removal of glucose residues from an oligosaccharide by contacting an α-glucosidase with a compound of Formula I or a salt thereof, a compound of Formula II or a salt thereof, or a mixture of any two or more thereof:

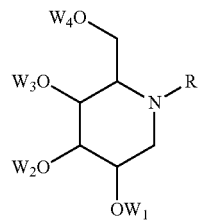

wherein R is:

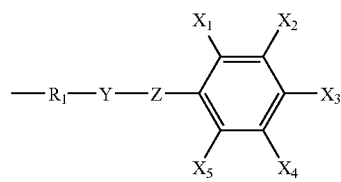

$R_1$ is a substituted or unsubstituted butyl, pentyl, hexyl, heptyl, or octyl group;
$W_{1-4}$ are independently selected from hydrogen, substituted or unsubstituted alkyl groups, substituted or unsubstituted haloalkyl groups, substituted or unsubstituted alkanoyl groups, substituted or unsubstituted aroyl groups, or substituted or unsubstituted haloalkanoyl groups;
$X_1$ is $NO_2$; $X_3$ is $NO_2$ or $N_3$; $X_2$, $X_4$ and $X_5$ are each H;
Y is a substituted or unsubstituted $C_1$-alkyl group other than carbonyl; and
Z is NH.

15. A compound of Formula I:

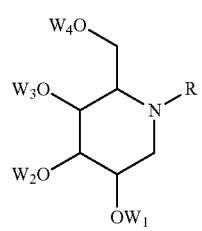

wherein R is:

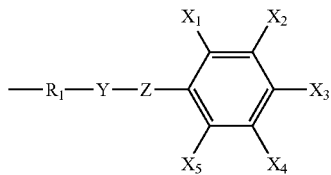

$R_1$ is a substituted or unsubstituted butyl, pentyl, hexyl, heptyl, or octyl group;
$W_{1-4}$ are independently selected from hydrogen, substituted or unsubstituted alkyl groups, substituted or unsubstituted haloalkyl groups, substituted or unsubstituted alkanoyl groups, substituted or unsubstituted aroyl groups, or substituted or unsubstituted haloalkanoyl groups;
$X_1$ is $NO_2$; $X_3$ is $NO_2$ or $N_3$; $X_2$, $X_4$, and $X_5$ are H;
Y is absent or is a substituted or unsubstituted $C_1$-alkyl group, other than carbonyl; and
Z is selected from a bond or NH;
provided that when Z is a bond, Y is absent, and
provided that when Z is NH, Y is a substituted or unsubstituted $C_1$-alkyl group, other than carbonyl.

16. The compound of claim 15, wherein Z is NH.
17. The compound of claim 15, wherein $X_3$ is $NO_2$.
18. The compound of claim 15, wherein $X_3$ is $N_3$.
19. The compound of claim 15, wherein $W_{1-4}$ are H.
20. The compound of claim 15, wherein Y is $CH_2$.
21. The compound of claim 15, wherein the compound of Formula I has the structure of the compound of Formula IA:

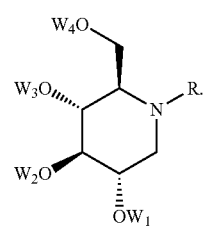

22. A composition comprising the compound of claim 15 and a pharmaceutically acceptable carrier.
23. A method for preparing a compound of Formula III

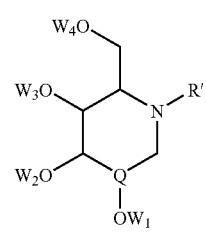

comprising condensing a compound of Formula IV:

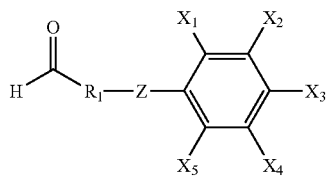

IV with a compound of Formula V

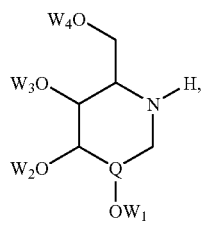

V wherein,
R' is:

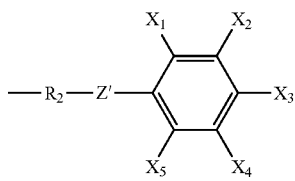

Q is CH,
R$_1$ is a substituted or unsubstituted butyl, pentyl, hexyl, heptyl, or octyl group;
R$_2$ is a substituted or unsubstituted alkyl group;
W$_{1-4}$ are independently hydrogen, substituted or unsubstituted alkyl groups, substituted or unsubstituted haloalkyl groups, substituted or unsubstituted alkanoyl groups, substituted or unsubstituted aroyl groups, or substituted or unsubstituted haloalkanoyl groups;
X$_1$ is NO$_2$; X$_3$ is NO$_2$ or N$_3$; X$_2$, X$_4$, and X$_5$ are H; and
Z' is selected from a bond or NH; to obtain the compound of Formula III.

24. The method of claim 23, wherein the condensation is by reductive amination of the compound of Formula VI with the compound of Formula V.

25. The method of claim 23, wherein the compound of Formula IV is prepared by aromatic fluorine displacement of a compound of Formula VI with HO—R$_2$—NH$_2$,

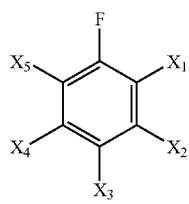

VI to form a compound of Formula VII,

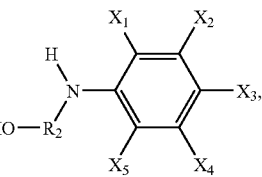

VII and oxidation of the compound of Formula VII to provide the compound of Formula IV.

26. The method of claim 23, wherein the compound of Formula III has a stereochemistry of a compound of Formula IIIA,

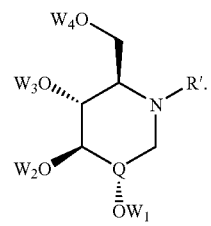

IIIA

27. A compound of Formula I:

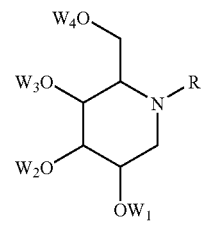

I wherein R is:

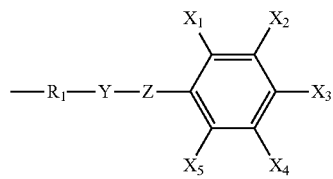

R$_1$ is a substituted or unsubstituted alkyl group;
W$_{1-4}$ are independently selected from hydrogen, substituted or unsubstituted alkyl groups, substituted or unsubstituted haloalkyl groups, substituted or unsubstituted alkanoyl groups, substituted or unsubstituted aroyl groups, or substituted or unsubstituted haloalkanoyl groups;
X$_1$ is NO$_2$; X$_3$ is NO$_2$ or N$_3$; X$_2$, X$_4$, and X$_5$ are H;
Y is absent or is a substituted or unsubstituted C$_1$-alkyl group, other than carbonyl; and
Z is selected from a bond or NH;
provided that when Z is a bond, Y is absent, and
provided that when Z is NH, Y is a substituted or unsubstituted C$_1$-alkyl group, other than carbonyl.

28. The compound of claim 27, wherein Z is NH.

29. The compound of claim 27, wherein $X_3$ is $NO_2$.

30. The compound of claim 27, wherein $X_3$ is $N_3$.

31. The compound of claim 27, wherein $W_{1-4}$ are H.

32. The compound of claim 27, wherein Y is $CH_2$.

33. The compound of claim 27, wherein the compound of Formula I has the structure of the compound of Formula IA:

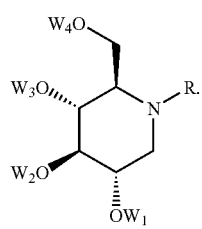

IA

34. A composition comprising the compound of claim 27 and a pharmaceutically acceptable carrier.

35. A method for preparing a compound of Formula III

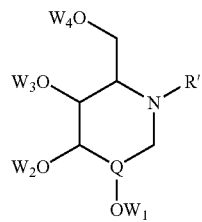

III comprising condensing a compound of Formula IV:

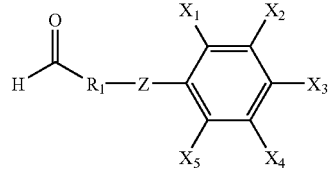

IV with a compound of Formula V

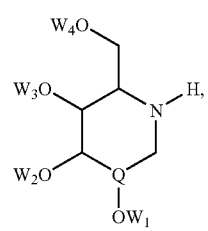

V wherein,

R' is:

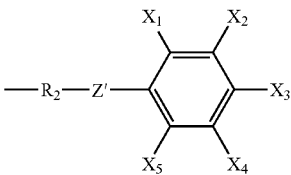

Q is CH, $R_1$ is a substituted or unsubstituted alkyl group;

$R_2$ is a substituted or unsubstituted alkyl group;

$W_{1-4}$ are independently hydrogen, substituted or unsubstituted alkyl groups, substituted or unsubstituted haloalkyl groups, substituted or unsubstituted alkanoyl groups, substituted or unsubstituted aroyl groups, or substituted or unsubstituted haloalkanoyl groups;

$X_1$ is $NO_2$; $X_3$ is $NO_2$ or $N_3$; $X_2$, $X_4$, and $X_5$ are H; and

Z' is selected from a bond or NH; to obtain the compound of Formula III.

36. The method of claim 35, wherein the condensation is by reductive amination of the compound of Formula VI with the compound of Formula V.

37. The method of claim 35, wherein the compound of Formula IV is prepared by aromatic fluorine displacement of a compound of Formula VI with HO—$R_2$—$NH_2$,

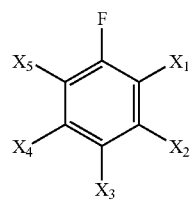

VI to form a compound of Formula VII,

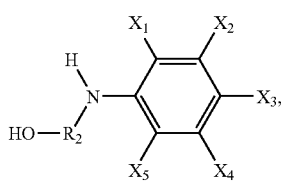

VII and oxidation of the compound of Formula VII to provide the compound of Formula IV.

38. The method of claim 35, wherein the compound of Formula iii has a stereochemistry of a compound of Formula IIIA,

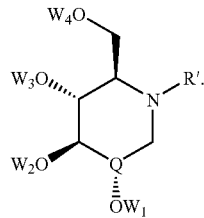

IIIA

* * * * *